US00PP30442P2

(12) United States Plant Patent
Heuger

(10) Patent No.: US PP30,442 P2
(45) Date of Patent: Apr. 23, 2019

(54) ***HELLEBORUS* PLANT NAMED 'COSEH 3140'**

(50) Latin Name: ***Helleborus niger* X *Helleborus* x *hybridus***
Varietal Denomination: COSEH 3140

(71) Applicant: Josef Heuger, Glandorf (DE)

(72) Inventor: Josef Heuger, Glandorf (DE)

( * ) Notice: Subject to any disclaimer, the term of this patent is extended or adjusted under 35 U.S.C. 154(b) by 0 days.

(21) Appl. No.: 15/732,561

(22) Filed: Nov. 27, 2017

(51) Int. Cl.
*A01H 5/02* (2018.01)

(52) U.S. Cl.
USPC ..... Plt./439

(58) Field of Classification Search
USPC ..... Plt./263.1, 439
See application file for complete search history.

*Primary Examiner* — Susan McCormick Ewoldt
*Assistant Examiner* — Karen M Redden
(74) *Attorney, Agent, or Firm* — C. A. Whealy

(57) ABSTRACT

A new and distinct cultivar of *Helleborus* plant named 'COSEH 3140', characterized by its upright and mounding plant habit; moderately vigorous growth habit; dark green-colored leaves; freely flowering habit; single purple-colored flowers; and good garden performance.

2 Drawing Sheets

Botanical designation: *Helleborus niger* X *Helleborus* x *hybridus*.

Cultivar denomination: 'COSEH 3140'.

BACKGROUND OF THE INVENTION

The present invention relates to a new and distinct cultivar of *Helleborus* plant, botanically known as *Helleborus niger* X *Helleborus* x *hybridus* and hereinafter referred to by the name 'COSEH 3140'.

The new *Helleborus* plant is a product of a planned breeding program conducted by the Inventor in Glandorf, Germany. The objective of the breeding program was to create new uniform *Helleborus* plants with unique and attractive plant habit, leaf and flower coloration and resistance to pests common to *Helleborus* plants.

The new *Helleborus* plant originated from a cross-pollination conducted by the Inventor in Glandorf, Germany in 2012 of a unnamed selection of *Helleborus niger*, not patented, as the female, or seed parent and an unnamed selection of *Helleborus* x *hybridus*, not patented, as the male, or pollen parent. The new *Helleborus* plant was discovered and selected by the Inventor as a single flowering plant from within the progeny of the stated cross-pollination grown in a controlled greenhouse environment in Glandorf, Germany in 2014.

Asexual reproduction of the new *Helleborus* plant by divisions in a controlled environment in Glandorf, Germany since 2015 has shown that the unique features of this new *Helleborus* plant are stable and reproduced true to type in successive generations.

SUMMARY OF THE INVENTION

Plants of the new *Helleborus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'COSEH 3140'. These characteristics in combination distinguish 'COSEH 3140' as a new and distinct *Helleborus* plant:

1. Upright and mounding plant habit.
2. Moderately vigorous growth habit.
3. Dark green-colored leaves.
4. Freely flowering habit.
5. Single purple-colored flowers.
6. Good garden performance.

Plants of the new *Helleborus* and the parent selections differ primarily in flower color as plants of the female parent selection have flowers that are solid white in color and plants of the male parent selection have flowers that are dark pink in color. In addition, plants of the new *Helleborus* are more freely flowering than plants of the female parent selection.

Plants of the new *Helleborus* can be compared to plants of *Helleborus orientalis* 'HLR 160', disclosed in U.S. Plant Pat. No. 21,504. In side-by-side comparisons, plants of the new *Helleborus* differ primarily from plants of 'HLR 160' in flower color as plants of 'HLR 160' have flowers with dense greyed purple-colored spots present on a large area of the sepals.

BRIEF DESCRIPTION OF THE PHOTOGRAPHS

The accompanying colored photographs illustrate the overall appearance of the new *Helleborus* plant showing the colors as true as it is reasonably possible to obtain in colored reproductions of this type. Colors in the photographs may differ slightly from the color values cited in the detailed botanical description which accurately describe the colors of the new *Helleborus* plant.

The photograph on the first sheet is a side perspective view of a typical flowering plant of 'COSEH 3140' grown in a container.

The photograph on the second sheet is a close-up view of a typical flower of 'COSEH 3140'.

DETAILED BOTANICAL DESCRIPTION

The aforementioned photographs and following observations, measurements and values describe plants grown during the winter in 15-cm containers in a glass-covered greenhouse in Glandorf, Germany and under cultural practices typical of commercial *Helleborus* production. During the production of the plants, day temperatures ranged from 12° C. to 24° C. and night temperatures ranged from 3° C. to 18° C. Plants were 14 months old when the photographs and the description were taken. In the following description, color references are made to The Royal Horticultural Society Colour Chart, 2015 Edition, except where general terms of ordinary dictionary significance are used.

Botanical classification: *Helleborus niger* X *Helleborus* x *hybridus* 'COSEH 3140'.

Parentage:

*Female, or seed, parent*.—Unnamed selection of *Helleborus niger*, not patented.

*Male, or pollen, parent*.—Unnamed selection of *Helleborus* x *hybridus*, not patented.

Propagation:

*Type*.—In vitro rhizome culture.

*Time to initiate roots, winter*.—About two months at temperatures about 12° C.

*Time to produce a rooted young plant, winter*.—About six months at temperatures ranging from 4° C. to 15° C.

*Root description*.—Thick to thin, fleshy; typically white to brown in color, actual color of the roots is dependent on substrate composition, water quality, fertilizer type and formulation, substrate temperature and physiological age of roots.

*Rooting habit*.—Sparse.

Plant description:

*Plant and growth habit*.—Herbaceous perennial; upright and mounding plant habit with flowers held above the foliar plane; plant shape, roughly flattened globular; moderately vigorous growth habit; moderate growth rate.

*Plant height, soil level to top of foliar plane*.—About 28.2 cm.

*Plant height, soil level to top of flowers*.—About 30.3 cm.

*Plant diameter* (*area of spread*).—About 45 cm.

Leaf description:

*Arrangement*.—Leaves arranged in a basal rosette; leaves palmately compound with typically seven leaflets per leaf.

*Leaf length*.—About 17.7 cm.

*Leaf width*.—About 21.8 cm.

*Leaflet length*.—About 11.5 cm.

*Leaflet width*.—About 5.8 cm.

*Leaf shape*.—Palmate; reniform in outline.

*Leaflet shape*.—Ovate, obovate to elliptic.

*Leaflet apex*.—Bluntly acute.

*Leaflet base*.—Attenuate.

*Leaflet margin*.—Finely serrate; lowest leaflets occasionally cleft.

*Leaflet texture and luster, upper surface*.—Smooth, glabrous; moderately leathery; moderately glossy.

*Leaflet texture and luster, lower surface*.—Smooth, glabrous; moderately leathery; slightly glossy.

*Leaflet venation pattern*.—Pinnate.

*Leaflet color*.—Developing leaflets, upper surface: Close to 137B. Developing leaflets, lower surface: Close to 147B. Fully developed leaflets, upper surface: Close to darker than between 139A and N189A; venation, close to 147B. Fully developed leaflets, lower surface: Close to 144A and 144B; venation, close to 144A.

*Petioles*.—Length: About 16.4 cm. Diameter: About 5 mm to 5.5 mm. Strength: Strong. Texture and luster, upper and lower surfaces: Smooth, glabrous; moderately glossy. Color, upper and lower surfaces: Close to 144A; proximally, moderately to heavily tinged and covered with small spots, close to 187A and 187B.

Flower description:

*Flower shape and habit*.—Single rotate flowers; arranged solitary or in small clusters with about four flowers each; freely flowering habit with about 72 flowers developing per plant; flowers facing outwardly to slightly nodding.

*Fragrance*.—None detected.

*Natural flowering season*.—Plants begin flowering about ten months after planting; plants flower during the winter in Germany.

*Flower longevity on the plant*.—About ten days; sepals persistent, other flower parts not persistent.

*Flower buds*.—Length: About 2 cm. Diameter: About 1.2 cm. Shape: Ovoid. Texture and luster: Smooth, glabrous; slightly glossy. Color: Close to between N77B and N186D; venation, close to 187A.

*Inflorescence height*.—About 12.9 cm.

*Inflorescence diameter*.—About 13 cm.

*Flower diameter*.—About 7.2 cm.

*Flower depth* (*height*).—About 3.4 cm.

*Petals*.—Transformed into nectaries.

*Sepals*.—Quantity and arrangement: About five, arranged in a single whorl. Length: About 4.7 cm. Width: About 4.1 cm. Shape: Broadly ovate, slightly concave. Apex: Obtuse. Base: Cuneate. Margin: Entire; very slightly undulate. Texture and luster, upper and lower surfaces: Smooth, glabrous; matte. Color: When opening, upper surface: Close to N77B. When opening, lower surface: Lighter than close to N77B; venation, close to 71A and 72A. Fully opened, upper surface: Close to N77B; distally, fading to lighter than N77B. Fully opened, lower surface: Lighter than close to N77B; venation, close to 71A and 72A.

*Flower bracts*.—Quantity per flower: Typically one. Length: About 6.3 cm. Width: About 4.8 cm. Shape: Trifoliate. Apex: Acute. Base: Broadly cuneate. Margin: Entire; slightly undulate. Color, upper surface: Close to 137B. Color, lower surface: Close to 147B; main vein, close to N186C.

*Peduncles*.—Length: About 24.3 cm. Diameter: About 8 mm to 10 mm. Aspect: About 10° from vertical. Strength: Strong. Texture and luster: Smooth, glabrous; moderately glossy. Color: Close to 144C; flushed and densely covered with small spots, close to 187B to 187C.

*Pedicels*.—Length: About 3.6 cm. Diameter: About 3 mm to 4 mm. Aspect: About 30° from peduncle axis. Strength: Moderately strong. Texture and luster: Smooth, glabrous; glossy. Color: Close to between 187A and 200B.

*Reproductive organs*.—Stamens: Quantity per flower: About 100. Filament length: About 1.3 cm. Filament color: Close to 186D. Anther shape: Reniform; basifixed. Anther size: About 1.75 mm by 2.5 mm.

Anther color: Close to 1C. Pollen amount: Scarce. Pollen color: Close to 4D. Pistils: Quantity per flower: About seven. Pistil length: About 8 mm. Stigma diameter: About 0.3 mm. Stigma shape: Club-shaped. Stigma color: Close to 157A. Style length: About 7.5 mm. Style color: Close to 187A. Ovary color: Close to 187A. Nectaries (transformed petals): Quantity per flower: About 13 to 15. Length: About 1.2 cm. Diameter: About 3 mm. Shape: Tubular, flattened. Texture and luster, inner and outer surfaces: Smooth, glabrous; matte. Color, immature, inner and outer surfaces: Close to N144A; mid-section, heavily tinged with close to 200C. Color, mature, inner and outer surfaces: Close to between 150B and 151B; mid-section, heavily tinged with close to 200C.

*Seeds and fruits*.—Seed and fruit development have not been observed on plants of the new *Helleborus* to date.

Garden performance: Plants of the new *Helleborus* have been observed to have good garden performance and to tolerate rain, wind and to be suitable for USDA Hardiness Zones 5 through 9.

Pathogen & pest resistance: Plants of the new *Helleborus* have not been observed to be resistant to pathogens and pests common to *Helleborus* plants to date.

It is claimed:

1. A new and distinct *Helleborus* plant named 'COSEH 3140' as illustrated and described.

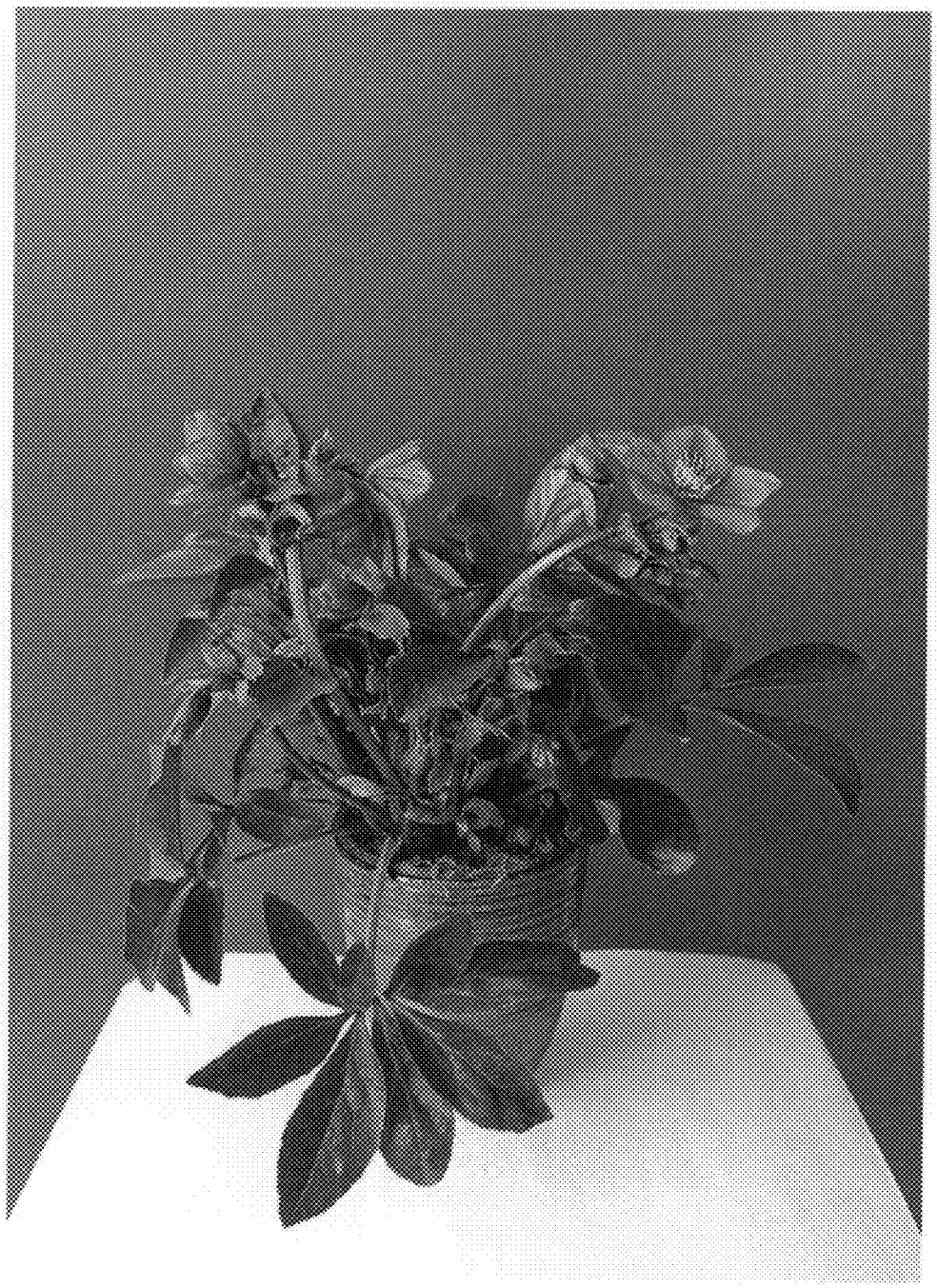

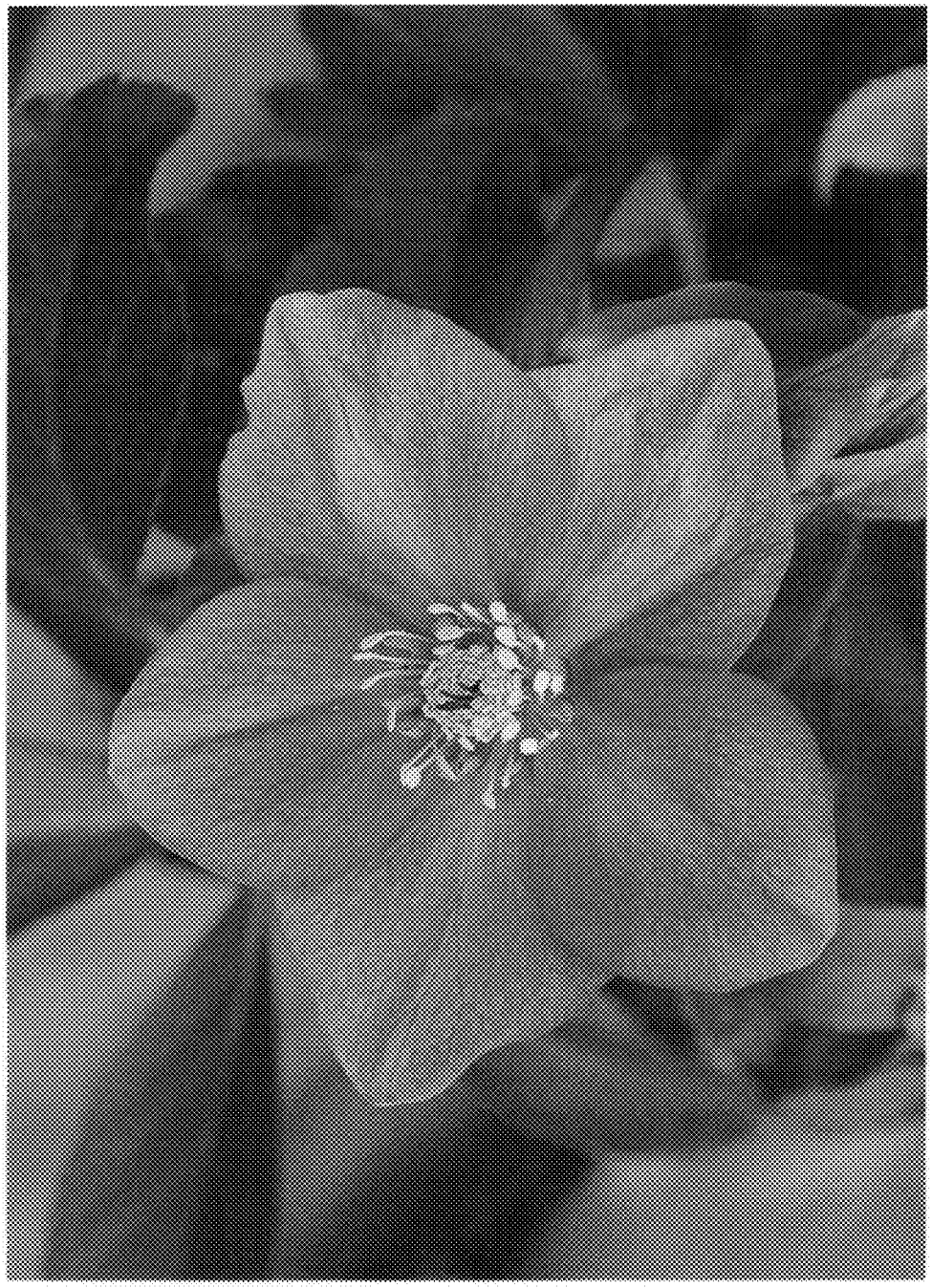

* * * * *